(12) United States Patent
Lang et al.

(10) Patent No.: US 6,358,051 B2
(45) Date of Patent: Mar. 19, 2002

(54) METHOD AND APPARATUS FOR DETERMINING THE PRELOAD FOR SCREWS FOR DENTAL IMPLANT SYSTEMS

(76) Inventors: Brien R. Lang, c/o ESPM, LLC, 4858 Gullane Dr., Ann Arbor, MI (US) 48103; Roman Gr. Maev; Andrei Ptchelintsev, both of c/o Technologies Decision Management Inc., 2899 Mangin Cres., Windsor, Ontario (CA)

(*) Notice: Subject to any disclaimer, the term of this patent is extended or adjusted under 35 U.S.C. 154(b) by 0 days.

(21) Appl. No.: 09/731,590

(22) Filed: Dec. 7, 2000

Related U.S. Application Data

(60) Provisional application No. 60/169,546, filed on Dec. 7, 1999.

(51) Int. Cl.[7] ............................. A61C 8/00; A61C 19/04
(52) U.S. Cl. ............................. 433/173; 433/72; 73/761
(58) Field of Search ................... 433/173, 174, 433/175, 176, 72, 27; 73/761

(56) References Cited

U.S. PATENT DOCUMENTS

| | | | | |
|---|---|---|---|---|
| 3,759,090 A | * | 9/1973 | McFaul et al. ............... | 73/761 |
| 4,686,859 A | * | 8/1987 | Wallace ....................... | 73/761 |
| RE34,686 E | * | 8/1994 | Coyle, Jr. et al. ............. | 73/761 |
| 5,343,759 A | * | 9/1994 | Hesthamar et al. ........... | 73/761 |
| 5,675,087 A | * | 10/1997 | MacLaugchlan et al. ..... | 73/761 |
| 6,204,771 B1 | * | 3/2001 | Ceney ......................... | 73/761 |

\* cited by examiner

*Primary Examiner*—Nicholas D. Lucchesi
(74) *Attorney, Agent, or Firm*—Welsh & Katz, Ltd.

(57) ABSTRACT

A method and apparatus are provided for determining the preload in a dental implant system. The preload is determined by transmitting a sonic impulse, which is preferably an ultrasonic impulse, at a predetermined frequency to the head of the implant screw through a transducer, which may be incorporated into the head of the screw, the head of a wand which generates the sonic impulse, or the transducer and pulse-generating instrumentation may be incorporated into a torque generating instrument used to tighten the screw. The preload is determined by measuring the delay between the first and second reflections through the preloaded screw to determine a preload value and comparing that value with a pre-established baseline value for the screw, and comparing the difference with a predetermined table of values to determine the preload on the screw.

14 Claims, 5 Drawing Sheets

FIG. 6

| WINDOW | FUNCTION |
|---|---|
| GAUGE CONFIGURATION<br>C:\CONFIG_STRAIN.GAG<br>N SAMPLES: 5000<br>N FRAMES: 1<br>N LEVELS: 255<br>CANCEL  OK | GAUGE CONFIGURATION:<br><br>SPECIFIES NUMBER OF SAMPLES AND NAME OF CONFIGURATION FILE<br>N SAMPLES CAN BE ANY OF TDS520 ACQUISITION LENGTHS.<br>N FRAMES MUST BE 1 (N SAMPLES>1 IS USED ONLY FOR FASTFRAME MODE N/A) |
| MEASUREMENT DIALOG<br>DEGREE/NS: 1<br>NEWTON/NS: 1<br>UNITS: PS<br>PRECISION: 0<br>CROSS AREA: 0<br>MAX LOAD: 0<br>OK  CANCEL | MEASUREMENT SETTINGS:<br><br>SPECIFIES COEFFICIENTS FOR STRAIN, TEMPERATURE, FORCE MEASUREMENT, PRECISION, MAXIMUM LOAD AND CROSS AREA OF THE SCREW DEGREE/NS- COEFFICIENT FOR TEMPERATURE NEWTONS/NS -COEFFICIENT FOR FORCE<br>UNITS-ONE OF THE FOLLOWING (PS, NS, N, MPa, DEGREE)<br>PRECISION-NUMBER OF SIGNIFICANT DIGITS AFTER DECIMAL POINT. (DEFAULT 2)<br>CROSS AREA OF THE SCREW IN $mm^2$ (DEFAULT 2.137)<br>MAX LOAD IS MAXIMUM TOF DEVIATION IN NANOSECONDS ALLOWED |

METHOD AND APPARATUS FOR DETERMINING THE PRELOAD FOR SCREWS FOR DENTAL IMPLANT SYSTEMS

This application claims benefit to Provisional Application No. 60/169,546 filed Dec. 7, 1997.

BACKGROUND

This invention was made with government support under grant No. 1R43DE13454 awarded by National Institutes of Health Office of Extramural Programs SBIR/STTR Grant Programs. The government has certain rights in the invention.

This invention relates to a method and apparatus for ensuring that small screws used to hold together dental implant components are tightened to the correct initial stress level, or "preload." According to the National Institute of Health, among the factors involved in the design of a dental implant are the forces produced during implant loading, the dynamic nature of loading, and the mechanical and structure properties of the prosthesis in stress transfer to tissues. Unfortunately, accurate data on such parameters are incomplete. *National Institutes of Health Consensus Development Conference Statement on Dental Implants.* Jun. 13–15, 1988.

During the early 1970's the dental profession was very hesitant to use dental implants or fixtures surgically implanted into a patient's jawbone as a treatment option to replace missing teeth. However, success with implants in the past 30 years has replaced this skepticism. This is due to the efforts of P-I Brånemark and co-workers in Sweden who introduced the concept of osseointegration in humans. When the principles of osseointegration are followed, the anchorage of a non-biological titanium implant unit to living bone will occur, with approximately 95% and 85% implant survival rates for the lower and upper jaws, respectively. See, for example in U.S. Pat. Nos. 4,824,372, 4,872,839 and 4,934,935 to Jorneus et al., Brajnovic and Edwards, respectively.

One of most critical aspects in the replacement of missing teeth using dental implants is the ability of small screws positioned within the implant complex to hold the various implant parts together during loading and stress transfer. As any screw in the implant system is tightened, the initial stress level developed within the screw becomes critical to the maintenance of the joint stability between the parts the screw is clamping together. Owing to the high strain level that the assembled joint experiences in everyday life, this initial stress level called the preload is of paramount importance. Insufficient tightening of a screw in the implant system can result in the screw becoming loose rather quickly, and over time this looseness can lead to fracture of the screw and potentially failure of the implant reconstruction. This is particularly critical for screws that secure spacers or abutments to the implant or fixture.

The stability of the screw joint is considered a function of the preload stress achieved in the screw when applying the preload tightening torque to clamp the implant components together. The optimum preload torque is influenced by the geometry of the screw, the contact relationships between the screw and its bore, between the screw and its threads, and between the bearing surfaces of the components clamped together by the screw, friction, and the properties of the materials used. One example is the joint formed between the bearing surface of the implant and the bearing surface of the spacer or abutment. Another example is the joint formed between a prosthesis and an abutment, also held together by a small screw in the implant system.

When the screw joint experiences instability, the screw will either loosen or fracture. Screw joint failure occurs in two stages. The first stage consists of external functional loading applied to the screw joint that gradually leads to the effective erosion of the preload in the screw joint. Any transverse or axial external force that causes a small amount of slippage between the threads releases some of the stress, and therefore, some of the preload is lost. The greater the preload applied to a screw joint up to a maximum equal to the proportional limit), the greater the resistance to loosening and the more stable the joint. As long as the frictional forces between the threads remain large, a greater external force will be required to cause loosening.

Once the critical load exceeds the screw joint preload, it becomes unstable. The external load rapidly erodes the remaining preload and results in vibration and micromovement that leads to the screw backing out. Once this second stage has been reached, the screw joint ceases to perform the function for which it was intended and has failed.

Optimizing the preload of a screw used in a dental implant system is critical for implant screw joint stability. As was stated earlier, implant screw loosening and fractures are quite common. The fact that on average complications with implant screw will occur in one out of every four implants surgically placed is significant. The need for optimum preload in screw tightening at the initial stages of implant component assembly and completion of the final implant restoration cannot be left to chance. An instrument that scientifically records the preload established in these implant screws following tightening and prior to any external load applications is essential to implant performance and the quality of life of the patient who receives implants as part of their dental rehabilitations.

It has been reported by Patterson and Johns that to achieve the maximum preload possible in component screws for dental implants, it is necessary to apply the appropriate tightening torque to each screw. Torque tightening devices for implant screws are discussed, for example, in U.S. Pat. No. 6,109,150 and 5,626,474. However, most screw torque-tightening devices lack accuracy because of a number of variables beyond the control of these conventional instruments. This means that the maximum stress developed in an implant screw tightened by conventional torque-tightening devices may be less than 70% of the yield strength of the screw itself and therefore well below the maximum possible preload for a stable joint. If the screw is loaded to the appropriate preload level one can be confident that the screw will not fail during the life of a patient when "normal" external loads are applied.

Ultrasound instrumentation has been used to measure the preload established in large bolts and screws in industrial applications. Thus far, however, it has not been applied to small screws the size of those used in implant systems. In industrial applications for large bolts and screws, the most common ultrasonic instruments for control of screw tension are called "pulse-echo" or "transit time" instruments. Bickford has described the use of this method with large bolts. A drop of fluid is placed on the head of the bolt to reduce the acoustic impedance between the transducer and bolt head. An acoustic transducer of some sort is placed against the bolt head. The instrument is then zeroed for this particular bolt because each bolt will have a slightly different acoustic length even if their physical lengths are the same. The zero load is recorded before tightening. Next, the bolt is tightened. If the transducer can remain in place during tightening, it will show the buildup of stretch or tension in the bolt during tightening. If it must be removed, it is repositioned on the bolt again after tightening to show the stress level achieved. If at some future time one wishes to measure the tension present within the bolt, the original data can be input to the instrument computer unit and after placing the transducer on the top of the bolt, the instrument will record the existing tension and the zero stress conditions.

In principle, the electronic instrument delivers a voltage pulse to the transducer, which emits a brief burst of ultrasound (typically five to seven or more cycles). This burst passes down through the bolt, echoes off the far end, and returns to the transducer. The electronic instrument measures very precisely the time delay required for the burst of sound to make its round trip in the bolt. As the bolt is tightened, the amount of time required for the ultrasound to make its round trip increased for two reasons: 1) the bolt stretches as it is tightened, so the path length increases, and 2) the average velocity of sound within the bolt decreases because the average stress level has increased. At low strain those functions can be approximated by linear ones of the preload in the bolt, so the total change in transit time is also a linear function of preload.

In dental implant technology, it is important to know what preload exists in implant screw joints at any time during implant therapy and throughout the life of the implant.

All of the currently used implant screws are fabricated from materials that are nontransparent and nonmagnetic. No other efficient technique for stress measurements of nonmagnetic and nontransparent materials is available. In contrast, a magnetic hysteresis curve can be used to infer the stress in magnetic materials, and also optical coherent methods can be used to infer the stress in transparent materials. However, the accuracy of this latter method is significantly lower than that of the ultrasonic TOF measurements, and as stated the implant screws are made of nonmagnetic materials. The use of mechanical methods for stress measurements requires exact measurements of the length of the implant parts, and with the 30 plus implant manufacturers throughout the world and their reluctance to provide this data, this method has definite limitations.

Ultrasonic measurement of the stress in a screw or bolt with a relatively big cross-section and length has been known for some time. Since the early fifties the technique has been theoretically and experimentally proven for a range of materials. Experimental and theoretical results obtained by Huges and Kelly on samples of rail steel with various load conditions have shown the proportionality between the uniaxial stress and velocity of acoustic waves. However, since then the method has been used for only relatively long and large cross-section components, partially due to an insufficient accuracy of TOF measuring devices. At present a digital oscilloscope's sampling rate ranging to several gigahertz makes possible a real time measurement of time intervals with the 10–100 picosecond accuracy. As to the dental implant screw in question, the ultrasonic evaluation of the stress via the time of flight measurement in principle is feasible. In practice the method is not straightforward and several factors have the potential to influence the accuracy, however, the whole performance is predictable. Difficulties reside in the small size transducer required (around 0.5 mm. active element diameter), and the small length inducing a low variation of the time of flight of the ultrasonic pulse. The smaller the transducer, the greater the exposure to a stronger mechanical stress. The smaller the length of the screw, the less variation in the time of flight and consequently the lower precision of the stress measurement obtained. Ambient temperature influencing elastic properties of materials, could also be a concern, which can be controlled.

The optimum preloads suggested for implant screw joints are a percentage of the yield strength of the screw. For example, 50–60% of yield has been suggested for average nongasketed joints, with "normal" safety or performance concerns. A 70–75% of yield has been suggested as the upper limit for nongasketed joints where "low preload" problems have been experienced in the past such as leaks, self-loosening, fatigue, etc. Joints which have had consistent "low preload" problems in the past, and where the need to avoid failure is significant and where service loads (or ignorance of service loads) make it unwise to take the screws any closer to the yield point, a 85–95% of yield has been suggested. Obviously, the preloads suggested for various screw joints demonstrate considerable variation, and depending on the joint requirements, the amount of preload achieved (% of the yield) would be significant in the performance of the joint. Furthermore, the amount of preload suggested depends on the accuracy of knowing the yield point of the screw. McGlumphy has reported significant differences between screws from several implant manufacturers even though the suggested tightening forces, and thus the preload achieved for these screws were the same. The force needed to cause failure in abutment screws for the systems as tested by McGlumphy ranged from 1.22 to 17.23 kg. However, even if the ultimate tensile strength of the screw, the proportional limit and the elastic range were known, neither the preload created by tightening using a torquing device suggested by the manufacturer for the particular screw nor the variability in the preload as a result of the tightening instrument used by the operator is known.

In summary, it would appear that a great deal of subjectivity exists in the tightening of implant screws. It isn't any wonder that screws loosen or fracture. The tightening instruments are a major variable. The quality and quantity of the tightening torque is in question. The "target" preload is uncertain. Finally, the achieved preload is unknown. In implant joints, which are very critical joint assemblies, the stability of the joint begins with knowing the exact preload achieved following the clamping together of the components. The Preload Measurement Gage will provide clinicians with that information.

SUMMARY OF THE INVENTION

This invention provides a method of determining the preload on a screw used in an implant system that secures a component to a fixture or to another component in a dental implant system which comprises the steps of transmitting a sonic impulse at a predetermined frequency to the head of the screw through a transducer when the screw is in an unstressed condition; measuring the delay between the first and second reflections through the unstressed screw, and establishing a baseline value for the unstressed screw; applying a preload of a predetermined value to the screw to secure the implant component in the implant system; transmitting a sonic impulse at a predetermined frequency to the head of the screw through a transducer; measuring the delay between the first and second reflections through the preloaded screw to establish a preload value; and determining the difference in the delay between the baseline value and the preload value, and comparing the difference with a predetermined table of values to determine the preload in the screw.

Transducers used in this invention may be any transducer that transmits and receives sonic impulses. Preferably, the sonic impulse is an ultrasonic impulse. The frequency of the impulse may vary depending on the material characteristics of the screw.

Screws used with this invention may be measured in this manner in the unstressed state before they are packaged and sold, and the baseline value may be provided with the sales information.

This invention also includes apparatus for determining the preload in a dental implant system that includes a fixture having one end adapted for osseointegration into a jawbone, the other end adapted to receive a spacer and including an internal bore that includes threads for engaging with a screw to secure the spacer to the implant, the spacer including an internal bore to receive the screw. The prosthesis may be attached to the implant system with a second screw. The apparatus comprises means for achieving a preload in the screw to secure the component in the implant system, which may be any conventional means, such as a hex wrench or screwdriver, as are commonly sold by companies such as Nobel Biocare, Implant Innovations, or others who market dental implants, abutments, and tools. The apparatus also includes means for transmitting a sonic impulse, which is preferably an ultrasonic impulse, at a predetermined frequency to the head of the screw through a transducer, which may be any apparatus that generates an ultrasonic impulse at the desired frequency. The frequency of the sonic impulse may vary, depending on the material and configuration of the screw. The apparatus also includes means for measuring the delay between the first and second reflections through the preloaded screw to determine a preload value, which may consist of a suitable measurement circuit, which may be in a separate control box, or part of a wand used to transmit and receive the ultrasonic impulse and pulses. The apparatus also includes means for determining the difference in the delay between a pre-established baseline value for the screw and the preload value, and comparing the difference with a predetermined table of values to determine the preload on the screw.

THE DRAWINGS

FIG. 6 is a diagram showing configuration windows that may be used with the present invention.

DETAILED DESCRIPTION

Figure 1:
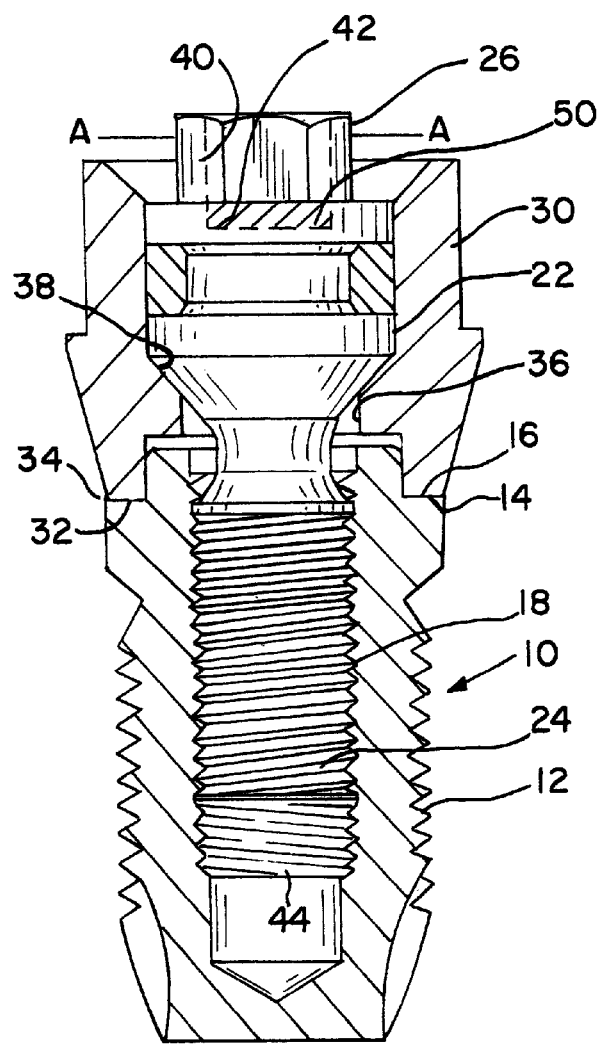
FIG. 1 is a sectional view of a dental implant installation of the prior art, adapted for purposes of this invention.
Figure 1A:
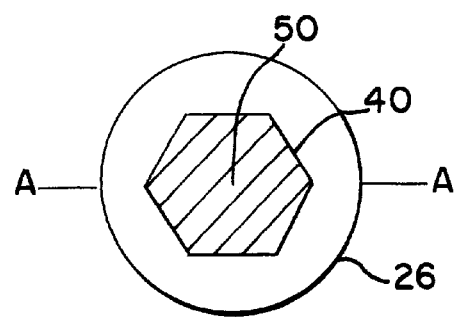
FIG. 1A is a sectional view taken along line A—A.

Implant systems, which are well known in the art, generally consist of an implant or fixture, which is surgically implanted into a patient's upper or lower jawbone. As shown in FIG. 1 and FIG. 1A, the fixture 10 includes an externally threaded body 12, which is surgically screwed into the jawbone. At one end of the body is a flange 14, which has bearing surface 16. Body 12 of fixture 10 includes an internal bore 18, which extends from the flange 14 and which is at least partially threaded to receive an abutment screw (also known as a spacer screw) 22, which includes a threaded portion 24, and a head 26. An abutment 30 includes a bearing surface 32, which forms a joint 34 with the bearing surface 16 of flange 14. Abutment 30 also includes an internal bore 36 to receive screw 22 and a flange 38 which is smaller in diameter than the head 26 of abutment screw 22. The abutment screw 22 passes through the bore 36 of abutment 30, and the threaded portion 24 of abutment screw 22 mates with the internal threads 20 of internal bore 18 of the fixture 10. Abutment screw 22 is screwed into the internally threaded bore 18 of fixture 10, and tightened to a predetermined preload to secure the abutment 30 to the fixture 10.

Head 26 of the abutment screw 22 is provided with an internal bore 40 which has a geometric shape, such as an internal hex, adapted to receive a tool such as a hex wrench for tightening the screw. Other geometric shapes for tools are well known in the art. The abutment screw used for practicing the invention is provided with a reflecting surface at the bottom 42 of bore 40. A second reflecting surface 44 is provided at the opposite end of the screw. Each reflecting surface is preferably generally flat, and generally perpendicular to the line of transmission of the sonic pulse. Any number of screw head designs may be used, so long as each end of the screw (heads and ends) has a reflecting surface that is sufficiently perpendicular to the ultrasound propagation pathway in order to register and record at a sufficient amplitude the time of flight between two acoustical impulses traveling the length of the screw. All dental implant screw designs can potentially be modified to create a sufficiently reflecting area within and at the base of the head alteration and also at the end of the screw for this purpose. Alternatively, other forms of reflecting surfaces may be used.

In one embodiment of the invention depicted in FIG. 1, a small 20 MHz PZT element (transducer) 50 of 0.8 mm diameter is fixed to a flattened area 42 in the head 26 of a screw 22. This transducer 50 provides the interface between the screw 22 and an acoustic source 70 (See FIG. 2) for the transmission of an acoustic pulse along the long axis of the screw.

Figure 2:
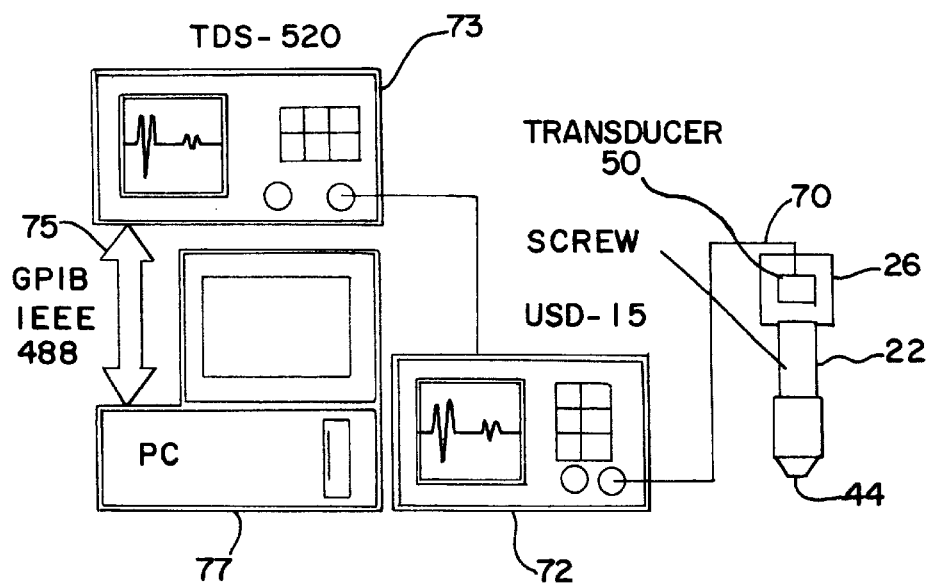
FIG. 2 is a block diagram of one embodiment of the apparatus of this invention.
Figure 7:
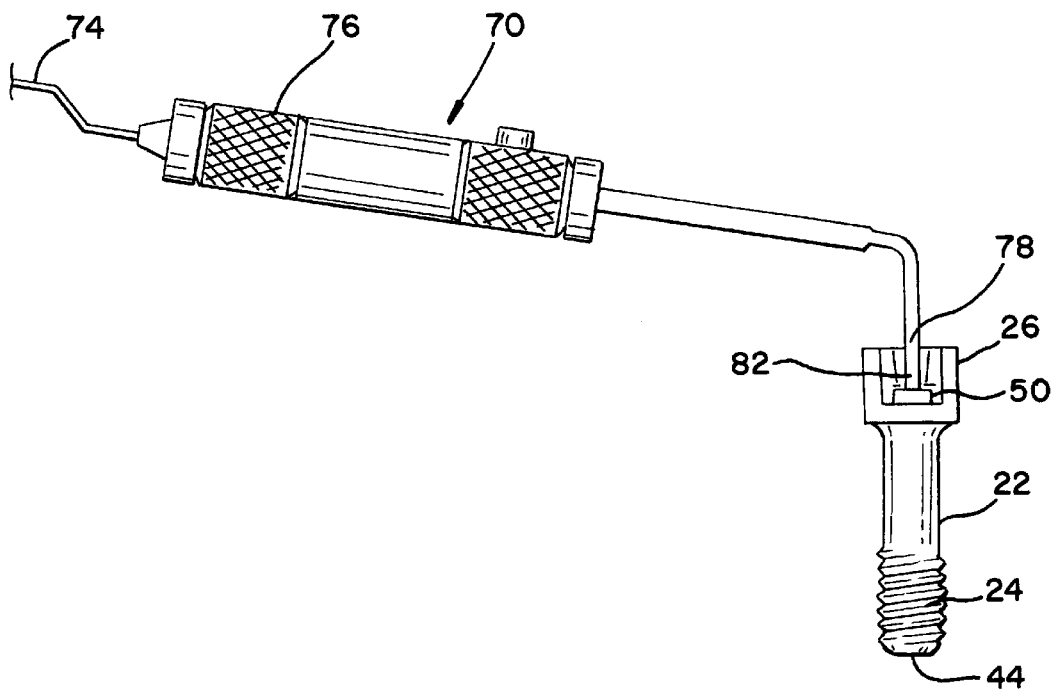
FIG. 7 shows a diagrammatic depiction of a wand that may be used with the present invention.

As shown in FIG. 7 and FIG. 2., the acoustic source is a hand held wand 70 that is electronically connected to a control box 72. The electronic connection may be hard-wired 74, or it may be accomplished remotely, such as by infrared or by so-called "bluetooth" technology, so long as the wand is provided with appropriate infrared transmission and/or receiving means. Alternatively, the control box can be provided in miniaturized form through microelectronics entirely within the handle 76 of the wand 70.

Within the control box 72 are the electronics needed to initiate an ultrasonic impulse from an acoustic source 78 near the small tip 82 of the wand 70. The tip 82 of the wand 80 is placed in contact with the transducer element 50 in the head 26 of the screw 22, which clamps together the abutment 30 and implant 10 to form the screw joint 38 of the implant assembly. A sound impulse is initiated from the tip 82 of the wand 80 and the sound is transmitted by the transducer 50 in the screw head 26 to the opposite end 44 of the screw 22. Two clear sequential echo-pulses are reflected from the screw bottom (end) back to the transducer and ultimately across the interface to the wand.

The time of flight between pulses 1 and 2 can be determined independent of the acoustic contact variations. The time of flight of the wave propagation through the screw is registered by the transducer 50 and the information is transmitted and processed in the control box 72 by a computer microchip. Tightening of the screw will produced variations in screw length related to the elastic properties of the screw. Screw length variations influence the time of flight of the ultrasonic pulse along the long axis of the screw. The differences in the time of flight recorded before and after screw tightening are used to compute the stress within the screw as a function of screw tightening. The stress is computed by the control box electronics, and displayed both graphically and digitally at the control box 72.

Figure 3:
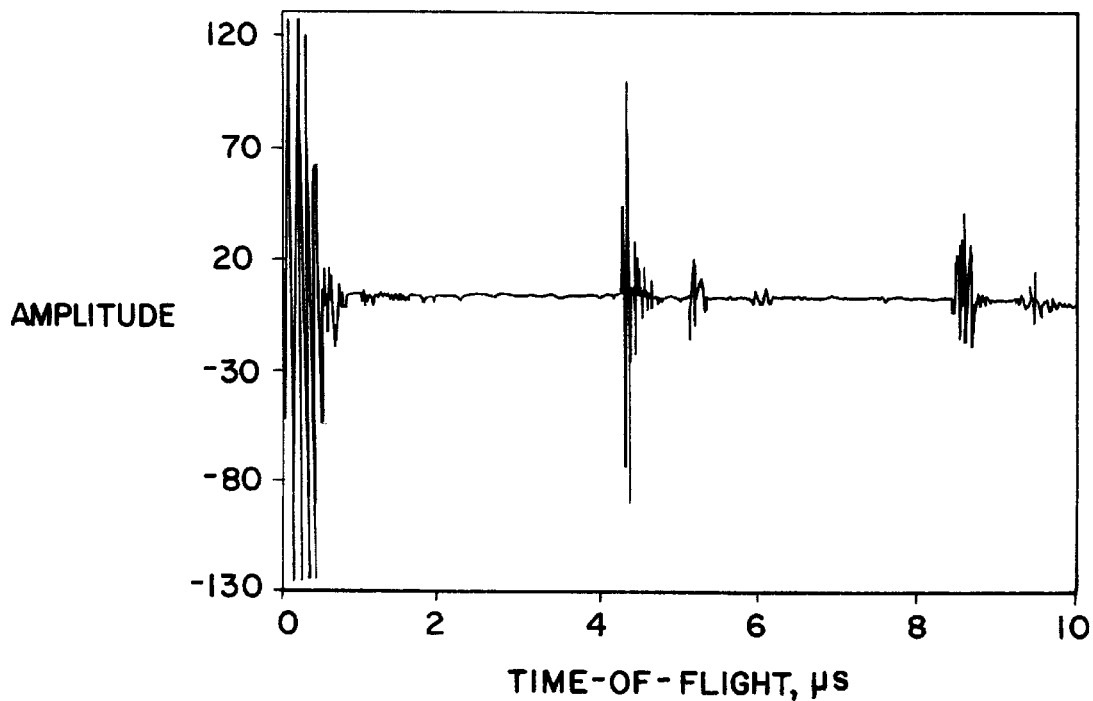
FIG. 3 is a typical A-scan pattern of pulses generated by this invention.
Figure 4:
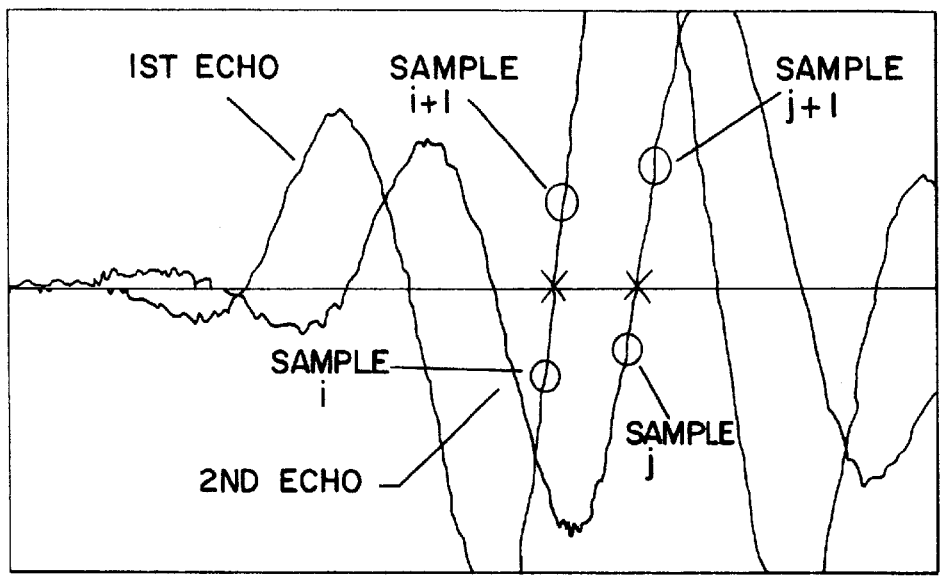
FIG. 4 is a diagram that demonstrates the principal of the time of flight.

As shown schematically in FIG. 2, a system for preload measurement may include, for example, an embedded 20 MHz ultrasonic transducer 50, an ultrasonic pulser-receiver USD-15 (Krautkramer) 72, a digitizing oscilloscope TDS-520 (Tektronix) 73 connected to a GPIB port (IEEE488) 75 with computer 77. As is discussed above, the implant screw is provided with a generally flattened surface inside the tool-receiving bore in order to accommodate a 1 mm diameter piezoelectric piston. A piezoelectric disk 50 is positioned inside the screw head and two wires soldered in order to provide the electric path. To protect the piezoelectric element and the wiring the head was molded with epoxy compound. The setup immediately provided two clear echo-reflections from the opposite end of the screw. To increase amplitude of the reflected signals the threaded end of the screw was slightly flattened. In FIG. 3 a typical A-scan is given. The basics of the measurement consist of determining variation of the delay between $1^{st}$ and $2^{nd}$ reflections. To measure the TOF between the two pulses zero cross-section method is used. The software seeks for the first minimum of both signals and then calculates the time coordinate of next zero cross-section linearly interpolating the signal between two consecutive samples for both first and second echo-pulses and finally estimates TOF as given by the following formula.

$$TOF = \frac{1}{f_{sampl}}\left(i - j + \left(\frac{wfm(i)}{wfm(i) - wfm(i+1)} - \frac{wfm(j)}{wfm(j) - wfm(j+1)}\right)\right), \quad (1)$$

where $f_{sampl}$ is the sampling frequency, wfm(k) is the digitized waveform data, i,j are samples around zero crossing (see FIG. 4). Better results are obtained at 1 GHz sampling rate. A real-time measurement provides ±0.2 ns precision, with 32-average mode the precision goes to 0.02 ns. This corresponds approximately to 0.025° C. temperature variation, or 0.6N force variation using for approximation elastic parameters of mild steel. Exact values of these uncertainties are to be calculated after the stress-TOF and temperature-TOF characteristics are studied for the material used in manufacturing the screw. This system results in excellent resolution of the method.

Figure 5:
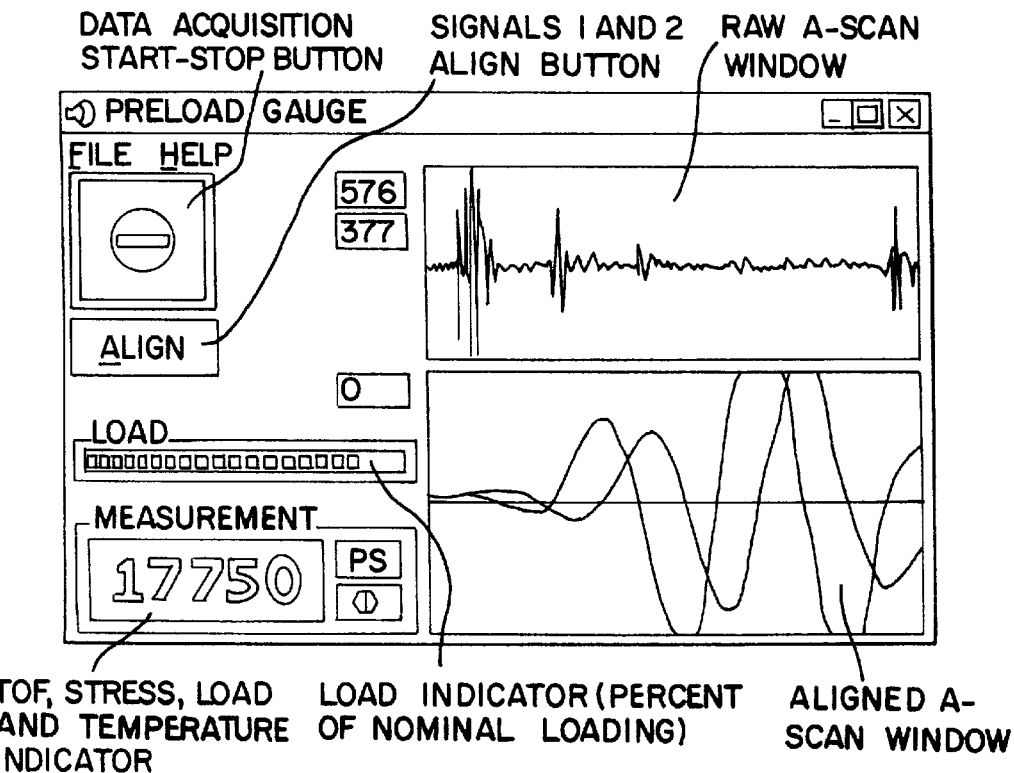
FIG. 5 is a depiction of a preload strain gauge program window for a computer program that may be used in the present invention.

To realize the measurement method a software program may be used. Basic features of the program are transfer of the digitized A-scan from TDS520 to a personal computer, serial port communication, time delay compensation and measurement, and data storage. The outlook of a program window is given in FIG. 5. Configuration windows for the preload gauge are shown in FIG. 6.

Figure 8:
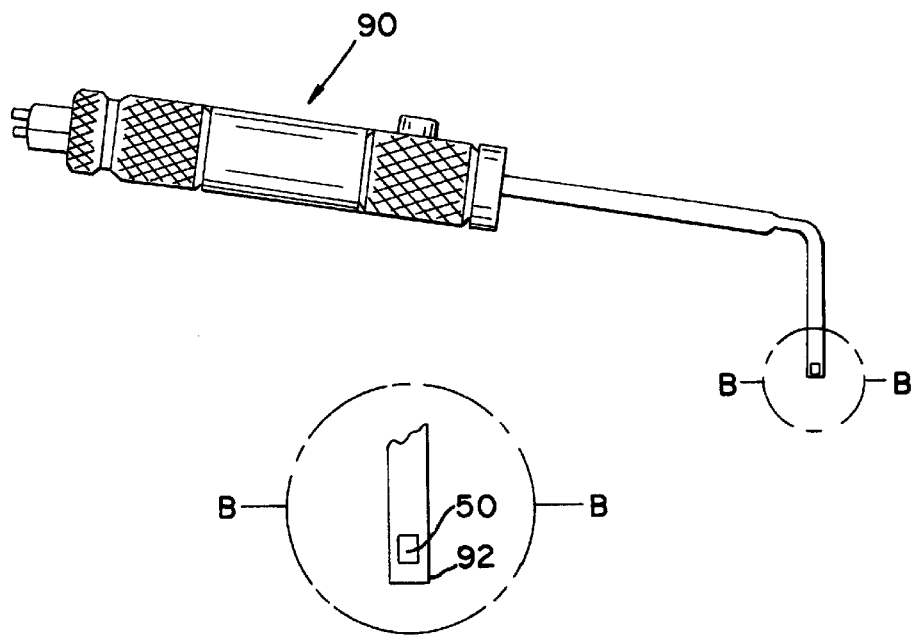
FIG. 8 is a diagrammatic depiction of a second type of wand that may be used with the present invention.

In another embodiment, depicted in FIG. 8, wand 90 is designed to transmit and receive acoustic and time of flight data without the need for contact between the wand tip and a transducer located in the head of the screw. In this embodiment, the transducer 50 is positioned within the tip 92 of the wand, near enough to the end to transmit and detect sonic impulses. The wand also incorporates technology for digital analog signals to be transmitted and received in order to carryout the functions identified in the hard-wired control box. The information received and transmitted by the wand may be displayed in a remotely located display mode.

In another embodiment, the ultrasonic transducer may be located within the tool used to tighten the screw. Thus, a screwdriver may be used to tighten the screw and either simultaneously or at the end of the torquing procedure measure the stress within the screw. One end of the screwdriver is formed in a well known latch-type design for attachment to an electronic or manual tightening torque apparatus. At the other end of the screwdriver, the ultrasonic transducer is positioned within the screwdriver end in a position permitting it to transmit and detect sonic impulses. The transducer is electronically connected to the latch-type end by internal circuitry. The transducer is electronically connected to either the electronic or manual tightening torque handpiece by an electronic interface within the handpiece head. The screwdriver is positioned in the screw bore and brought into intimate contact with the screw. Following initiation of the sound impulse, the sound travels through the screw to the end of the screw. In the electronic tightening torque apparatus, the time of flight of the wave propagation through the screw is registered by the transducer in the screw driver, and the information is transferred electronically back to the tightening torque apparatus control boxes or an associated display unit. The elastic properties of the screw, which have been altered by the torquing force used to tighten the screw, are displayed both graphically and digitally at the control box (6) as the preload.

In the case of the manual tightening torque apparatus, the electronics for initiation of the wave impulse from the screwdriver, and data retrieval and processing are located in a modified handle for the tightening torque apparatus. The registration, recording and computation of the time of flight are performed using micro-processing technology and transferring the information from the electronic port in the manual tightening torque handle (2) as a digital analog signal to a remote display unit.

We claim:

1. A method of determining the pre-load on a screw that secures a component to other components in a dental implant system comprising:
   a. Transmitting a sonic impulse at a predetermined frequency to the head of the screw through a transducer when the screw is in an unstressed condition;
   b. Measuring a first delay between first and second reflections through the unstressed screw, and establishing a baseline value for the unstressed screw;
   c. Applying a preload of a predetermined value to the screw to secure implant components together;
   d. Transmitting a sonic impulse at a predetermined frequency to the head of the preloaded screw through a transducer;
   e. Measuring a second delay between the first and second reflections through the preloaded screw to establish a preload value; and
   f. Determining the difference between the first delay and the second delay to establish a difference between the baseline value and the preload value, and comparing the difference with a predetermined table of values to determine the preload on the screw.

2. The method of claim 1 wherein the sonic impulse is an ultrasonic impulse.

3. The method of claim 1 wherein the screw secures an abutment to an implant.

4. The method of claim 1 wherein the screw secures a dental prosthesis to an abutment.

5. The method of claim 1 wherein the screw secures a dental prosthesis directly to an implant.

6. Apparatus for determining the preload on a screw in a dental implant system that includes at least one screw for securing components of the dental implant system together, wherein the dental implant system includes at least a fixture having one end adapted for osseointegration into a jawbone, the other end adapted to receive an abutment, and the abutment adapted to receive and support a dental prosthesis, the apparatus further comprising a. Means for applying a preload to the screw to secure at least some components of the implant system together;
   b. Means for transmitting a sonic impulse at a predetermined frequency to the head of the screw;
   c. Means for transmitting the sonic impulse through the screw and detecting first and second reflections of the pulses;
   d. Means for measuring the delay between the first and second reflections through the preloaded screw to determine a preload value; and
   e. Means for determining the difference in the delay between a pre-established baseline value for the screw and the preload value, and comparing the difference with a predetermined table of values to determine the preload on the screw.

7. The apparatus of claim 1 wherein the sonic impulse is an ultrasonic impulse.

8. The apparatus of claim 1 wherein the screw secures an abutment to an implant.

9. The apparatus of claim 1 wherein the screw secures a dental prosthesis to an abutment.

10. The apparatus of claim 1 wherein the screw secures a dental prosthesis directly to an implant.

11. The apparatus of claim 1 wherein the means for transmitting a sonic impulse is an apparatus that produces an ultrasonic impulse.

12. The apparatus of claim 1 wherein the means for transmitting the sonic impulse through the screw and detecting first and second reflections of the pulses is a transducer.

13. The apparatus of claim 12 wherein the transducer is affixed to the head of the screw.

14. The apparatus of claim 12 wherein the transducer is affixed to a wand, and the wand is in electronic communication with an electronic control and measurement circuit.

* * * * *